(12) United States Patent
Barba et al.

(10) Patent No.: US 8,734,765 B2
(45) Date of Patent: May 27, 2014

(54) COMPOSITIONS BASED ON POLYESTER IN AN OILY PHASE AND USES THEREOF

(75) Inventors: Claudia Barba, Paris (FR); Audrey Ricard, Saint-Maur-des-Fosse (FR)

(73) Assignee: L'Oreal, Paris (FR)

( * ) Notice: Subject to any disclaimer, the term of this patent is extended or adjusted under 35 U.S.C. 154(b) by 289 days.

(21) Appl. No.: 12/995,609

(22) PCT Filed: May 29, 2009

(86) PCT No.: PCT/EP2009/056611
§ 371 (c)(1),
(2), (4) Date: Dec. 1, 2010

(87) PCT Pub. No.: WO2009/147089
PCT Pub. Date: Dec. 10, 2009

(65) Prior Publication Data
US 2011/0085997 A1    Apr. 14, 2011

Related U.S. Application Data

(60) Provisional application No. 61/060,489, filed on Jun. 11, 2008.

(30) Foreign Application Priority Data

Jun. 2, 2008 (FR) ...................................... 08 53631

(51) Int. Cl.
*A61Q 1/04* (2006.01)
*A61Q 1/06* (2006.01)
*A61Q 1/08* (2006.01)
*A61Q 1/10* (2006.01)
*A61Q 1/12* (2006.01)

(52) U.S. Cl.
USPC ........... 424/64; 424/61; 424/70.7; 424/78.03; 424/401

(58) Field of Classification Search
None
See application file for complete search history.

(56) References Cited

U.S. PATENT DOCUMENTS

| 2004/0175338 | A1* | 9/2004 | Filippi et al. .................... 424/64 |
| 2005/0063926 | A1 | 3/2005 | Bathina et al. |
| 2011/0002869 | A1* | 1/2011 | Barba et al. .............. 424/70.121 |

FOREIGN PATENT DOCUMENTS

| EP | 0 991 691 | | 1/2003 |
| EP | 2 008 648 | | 12/2008 |
| JP | 2002 275020 | | 9/2002 |
| JP | 2004-256515 | * | 9/2004 |
| WO | WO 2007/066309 A2 | | 6/2007 |

OTHER PUBLICATIONS

International Search Report issued Nov. 4, 2009 in PCT/EP09/56611 filed May 29, 2009.
Office Action issued May 28, 2012 in Chinese Application No. 200980129775.6 (With English Translation).

* cited by examiner

*Primary Examiner* — Jyothsna Venkat
(74) *Attorney, Agent, or Firm* — Oblon, Spivak, McClelland, Maier & Neustadt, L.L.P.

(57) ABSTRACT

The present invention relates to a cosmetic make-up or care composition comprising an oily phase comprising at least one liquid polyester obtained by condensation of unsaturated fatty acid dimer and/or trimer and diol, said composition being free from lipophilic gelling agent or comprising at the most 10 wt. % thereof, relative to the weight of the composition. The present invention also relates to a method of make-up of the face and body comprising the use of said composition.

10 Claims, No Drawings

COMPOSITIONS BASED ON POLYESTER IN AN OILY PHASE AND USES THEREOF

This application is a National Stage of PCT/EP09/056611 filed May 29, 2009 and claims the benefit of U.S. 61/060,489 filed Jun. 11, 2008 and FR 0853631 filed Jun. 2, 2008.

The present invention relates to a cosmetic make-up or care composition comprising an oily phase comprising at least one liquid polyester obtained by condensation of unsaturated fatty acid dimer and/or trimer and of diol, said composition being free from lipophilic gelling agent or containing at the most 10 wt. % thereof relative to the weight of the composition. The present invention also relates to a method of make-up of the face and body comprising the use of said composition.

It is common to find, in cosmetic or dermatological products, a structured liquid phase, namely gelled and/or stiffened. This is in particular the case in solid compositions, especially solid cast compositions, lip balms, lipsticks, eye shadows, concealers and cast foundations, or gelled compositions, such as lip glosses. This structuring can be obtained using waxes, fillers, mineral silica or pyrogenic silica, which is hydrophobic, for example. The structuring can also be obtained with compounds which contribute consistency to the cosmetic composition by virtue of their high viscosity, such as sucrose esters. However, the formulations thus obtained are not completely satisfactory in terms of texture and also exhibit the disadvantage of being excessively slippery with an excessively greasy structure and, in the case of a coloured composition, the distribution of the colour may prove to be heterogeneous after application. Furthermore, in order to improve the persistence of the deposit on the lips, use is generally made of gloss oils, which are viscous. These gloss oils exhibit the disadvantage of being very sticky and thus not very comfortable. In addition, the gloss of the cosmetic compositions structured with mineral silica or waxes is not completely satisfactory in view of their mattifying aspect.

The present invention results more particularly from the surprising observation by the inventors that an oily phase can be structured by a liquid polyester obtained by condensation of unsaturated fatty acid dimer and/or trimer and diol, as with a gelling agent conventionally used for this purpose. Thus, it is no longer necessary to add a large amount of lipophilic gelling agents. In addition, the cosmetic make-up or care composition comprising said oily phase comprising said liquid polyester exhibits the advantage of being pleasant when applied and not very sticky while exhibiting little or no migration. It also exhibits a homogeneous appearance with an entirely satisfactory distribution in the colour, while exhibiting a high gloss and an improved durability of the gloss and of the colour over time. The compositions of the invention thus exhibit a particularly satisfactory appearance while being particularly comfortable.

SUMMARY OF THE INVENTION

The invention therefore relates to a cosmetic or skin care composition comprising an oily phase, in particular a liquid oily phase, comprising at least one liquid polyester obtained by condensation of unsaturated fatty acid dimer and/or trimer and of diol, said composition being free from lipophilic gelling agent or containing at the most 10 wt. % thereof relative to the weight of the composition.

The invention also relates to a method of make-up or of care of the skin, lips and/or of the integumentary appendages, comprising the application on these parts of a composition according to the invention.

DETAILED DESCRIPTION

The present invention relates to a cosmetic make-up or care composition comprising an oily phase comprising at least one liquid polyester obtained by condensation of unsaturated fatty acid dimer and/or trimer and of diol, said composition being free from lipophilic gelling agent or containing at the most 10 wt. % thereof relative to the weight of the composition.

The composition according to the invention can notably take the form of a foundation, a blusher or eye shadow, a concealer, a blush, a loose or compacted powder, a lipstick, a lip balm, a lip gloss, a lip or eye pencil, a mascara, an eyeliner, a nail varnish or a product for make-up of the body or for colouring the skin.

Preferably, the cosmetic or skin care composition according to the invention is a lipstick or a lip gloss.

The various constituents of the composition according to the invention are detailed below.

Polyester

The composition according to the invention includes at least one liquid polyester obtained by condensation of unsaturated fatty acid dimer and/or trimer and of diol.

The inventors have observed that such polyesters exhibit advantageous properties like lipophilic gelling agents conventionally used to structure the oily phases of cosmetic products. It has in particular been observed that the structure obtained with these polyesters is satisfactory as particularly pleasant during application and not very sticky while exhibiting little or no migration. The cosmetic compositions obtained with the polyester of the invention are thus particularly comfortable.

"Liquid polyester" means a polyester that begins to flow under its own weight in less than one minute at room temperature (25° C.).

"Unsaturated fatty acids" means, within the context of the present invention, mono- or polyunsaturated fatty acids having from 14 to 22 carbon atoms. The unsaturated fatty acid dimers can notably contain from 2 to 4 unsaturations in their carbon chain. The unsaturated fatty acid trimers can contain from 3 to 6 unsaturations in their carbon chain. Preferably, the unsaturated fatty acid dimers and/or trimers are polycarboxylic acids comprising at least 2 and up to 6 carboxylic acid functions per molecule. In a preferred embodiment, the unsaturated fatty acid dimer can contain from 28 to 44 carbon atoms and 2 carboxylic acid functions. The unsaturated fatty acid trimer can contain from 42 to 66 carbon atoms and 3 carboxylic acid functions. Preferably, an unsaturated fatty acid dimer is used, in particular having 36 carbon atoms and 2 carboxylic acid functions.

Mixtures of unsaturated fatty acid dimers and trimers and/or of unsaturated fatty acid (not polymerized, therefore corresponding to a monomer) can also be employed within the scope of the invention. In the case of such a mixture, preference is given to a mixture containing more than 50 wt. % of dimers, for example a mixture containing more than 90 wt. %, preferably more than 95%, of acids in the form of dimers, and the rest of the mixture can be trimers and/or monomers of unsaturated fatty acids.

The unsaturated fatty acid dimer and/or trimer can optionally be hydrogenated after the reaction of polymerization of the unsaturated fatty acid, notably to improve the stability of the dimer or trimer product.

Dimers of hydrogenated fatty acids (oleic or linoleic acid) are notably marketed under the brand names EMPOL1008, EMPOL1004, EMPOL1025, EMPOL1011 and EMPOL1062 by Cognis, and Pripol 1006 (dilinoleic acid) by Uniqema, International. Uniqema also markets a dimer of hydrogenated fatty acids under the designation Pripol 1013 (hydrogenated dilinoleic acid).

Particularly preferably, the unsaturated fatty acid dimer is a dimer of linoleic acid, also called dilinoleic acid, obtained by intermolecular polymerization of linoleic acid.

The unsaturated fatty acid can be of natural, preferably vegetable, origin. A fatty acid of vegetable origin can come from any vegetable source producing said fatty acid. For example, in the case of linoleic acid, it will be possible to use molecules extracted from soya or colza.

The polyester in the composition according to the invention is therefore obtained by condensation of a long-chain fatty acid polymerized with a diol. Within the scope of the present invention, "diol" denotes a C2 to C10, preferably C2-C8, and more preferably C2-C6, hydrocarbon compound, the carbon chain of which is substituted with two hydroxyl functions. The hydrocarbon chain or chains can be interrupted by an oxygen atom. The diols that can be used according to the invention can be linear, branched or cyclic, saturated or unsaturated alcohols. Preferably, the diol is a saturated linear diol. Particularly preferably, the diol is a butanediol, notably 1,2-butanediol, 1,3-butanediol or 1,4-butanediol, and preferably 1,4-butanediol.

Advantageously, the polyester used in the composition according to the invention has an average molecular weight between 500 and 2000, preferably between 1000 and 2000, and more preferably between 1200 and 1800.

In a particularly preferred embodiment, the polyester obtained by condensation of unsaturated fatty acid dimer and/or trimer and of diol is a polymer, or polyester, of dilinoleic acid and 1,4-butanediol, preferably having an average molecular weight of 1300, a viscosity at 40° C. of 2500-3500 cSt and a refractive index at 25° C. of 1.475-1.485. In this connection we may notably mention the polymer marketed by Biosynthis under the designation Viscoplast 14436H (INCI name: dilinoleic acid/butanediol copolymer).

The amount of polyester in the composition according to the invention can vary over a wide range and notably depends on the desired galenical and on the desired effects. It depends in particular on the desired gelling nature. Advantageously, to give an order of magnitude, the amount of polyester is between and 60 wt. %, preferably between 8 and 50 wt. % relative to the total weight of the composition.

Oily Phase

The composition according to the invention includes an oily phase that comprises one or more oils and/or a fat. It is in particular a liquid oily phase based on at least one oil, for example for the formulation of a composition for lip gloss. It can also be a solid fat, optionally mixed with oils, notably for a lipstick composition, in the form of a stick.

1. Liquid Oily Phase

Non-Volatile Oils

The oily phase of the composition according to the invention can comprise at least one non-volatile oil.

The non-volatile oils can be hydrocarbon oils and/or silicon oils and/or fluorinated oils.

The term "oil" means a non-aqueous compound which is immiscible with water and which is liquid at ambient temperature (25° C.) and atmospheric pressure (760 mmHg).

The term "non-volatile oil" means an oil which remains on keratinous substances at ambient temperature and atmospheric pressure for at least several hours and which has in particular a vapour pressure of less than $10^{-3}$ mmHg (0.13 Pa). A non-volatile oil can also be defined as having a rate of evaporation such that, under the conditions defined above, the amount evaporated at the end of 30 minutes is less than 0.07 mg/cm$^2$.

These oils can be of vegetable, mineral or synthetic origin.

The term "hydrocarbon oil" means an oil formed essentially, indeed even composed, of carbon and hydrogen atoms and optionally of oxygen or nitrogen atoms and which does not comprise a silicon or fluorine atom. It can comprise alcohol, ester, ether, carboxylic acid, amine and/or amide groups.

The term "silicone oil" means an oil comprising at least one silicon atom and in particular comprising Si—O groups.

Mention may in particular be made, as non-volatile hydrocarbon oil, of:

hydrocarbon oils of vegetable origin, such as triglycerides composed of esters of fatty acids and of glycerol, the fatty acids of which can have chain lengths varying from $C_4$ to $C_{24}$, it being possible for these acids to be linear or branched and saturated or unsaturated, such as the triglycerides of heptanoic or octanoic acids; these oils are in particular wheat germ, sunflower, grape seed, sesame, maize, apricot, castor, shea, avocado, olive, soybean, sweet almond, palm, rapeseed, cottonseed, hazelnut, macadamia, jojoba, alfalfa, poppy, pumpkinseed, cucumber, black-currant seed, evening primrose, millet, barley, quinoa, rye, safflower, candlenut, passionflower or musk rose oils; or also the triglycerides of caprylic/capric acids, such as those sold by Stéarineries Dubois or those sold under the "Miglyol 810®", "812®" and "818®" names by Dynamit Nobel, synthetic ethers;

linear or branched hydrocarbons of mineral or synthetic origin, such as liquid paraffin or its derivatives, liquid petrolatum, polydecenes, hydrogenated polyisobutene, such as Parléam®, sold by Nippon Oil Fats, squalane and mixtures thereof;

esters of a fatty acid, in particular of 4 to 22 carbon atoms, and in particular of octanoic acid, of heptanoic acid, of lanolic acid, of oleic acid, of lauric acid or of stearic acid, such as propylene glycol dioctanoate, propylene glycol monoisostearate, polyglyceryl-2 diisostearate or neopentyl glycol diheptanoate, synthetic esters, such as the oils of formula $R_1COOR_2$ in which $R_1$ represents the residue of a linear or branched fatty acid comprising from 1 to 40 carbon atoms and $R_2$ represents a hydrocarbon chain, in particular a branched hydrocarbon chain, comprising from 1 to 40 carbon atoms, provided that $R_1+R_2$ is ≥11, such as, for example, Purcellin oil (cetearyl octanoate), isononyl isononanoate, $C_{12}$ to $C_{15}$ alkyl benzoate, 2-ethylhexyl palmitate, 2-octyldodecyl stearate, 2-octyldodecyl erucate, isostearyl isostearate, 2-octyldodecyl benzoate, octanoates, decanoates or ricinoleates of alcohols or of polyalcohols, isopropyl myristate, isopropyl palmitate, butyl stearate, hexyl laurate, diisopropyl adipate, 2-ethylhexyl palmitate, 2-hexyldecyl laurate, 2-octyl-decyl palmitate, 2-octyldodecyl myristate, di(2-ethylhexyl) succinate, diisostearyl malate or isodecyl neopentanoate;

hydroxylated esters, such as isostearyl lactate, octyl hydroxystearate, octyldodecyl hydroxystearate, diisostearyl malate, triisocetyl citrate, glyceryl triisostearate, diglyceryl triisostearate or diethylene glycol diisononanoate; and pentaerythritol esters; esters of aromatic acids and of alcohols comprising from 4 to 22 carbon atoms, in particular tridecyl trimellitate, fatty alcohols which are liquid at ambient temperature and which have a branched and/or unsaturated carbon chain having from 8 to 26 carbon atoms, such as oleyl alcohol, linoleyl alcohol, linolenyl alcohol, isostearyl alcohol or octyl-dodecanol;

higher $C_8$-$C_{26}$ fatty acids, such as oleic acid, linoleic acid, linolenic acid or isostearic acid;

and mixtures thereof.

In particular, the composition according to the invention comprises at least one non-volatile ester oil.

Preferably, the non-volatile ester oil is a hydrocarbon ester oil.

Advantageously, the hydrocarbon ester oil has a viscosity of less than 15 cSt.

Preferably, the non-volatile ester oil of the composition is selected from synthetic esters, such as the oils of formula $R_1COOR_2$ in which $R_1$ represents the residue of a linear or branched fatty acid comprising from 1 to 40 carbon atoms and $R_2$ represents a hydrocarbon chain, in particular a branched hydrocarbon chain, comprising from 1 to 40 carbon atoms, provided that $R_1+R_2$ is $\geq 11$, such as, for example, Purcellin oil (cetearyl octanoate), isononyl isononanoate, $C_{12}$ to $C_{15}$ alkyl benzoate, 2-ethylhexyl palmitate, 2-octyldodecyl stearate, 2-octyldodecyl erucate, isostearyl isostearate, 2-octyldodecyl benzoate, octanoates, decanoates or ricinoleates of alcohols or of polyalcohols, isopropyl myristate, isopropyl palmitate, butyl stearate, hexyl laurate, diisopropyl adipate, 2-ethylhexyl palmitate, 2-hexyldecyl laurate, 2-octyl-decyl palmitate, 2-octyldodecyl myristate, di(2-ethylhexyl) succinate, diisostearyl malate or isodecyl neopentanoate.

Advantageously, the oily phase of the composition according to the invention comprises from 0.1 to 60 wt. % of oil or of ester oils, preferably from 5 to 50 wt. %.

The non-volatile silicone oils which can be used in the composition according to the invention can be phenylated silicone oils (the term phenylated silicone means an organopolysiloxane substituted by at least one phenyl group), non-volatile polydimethylsiloxanes (PDMSs), or polydimethylsiloxanes comprising pendant alkyl or alkoxy groups and/or alkyl or alkoxy groups at the end of the silicone chain, which groups each have from 2 to 24 carbon atoms.

The non-volatile oil can be present in a content ranging from 0.1 to 80 wt. %, preferably from 1 to 60 wt. %, better still from 5 to 50 wt. %, relative to the total weight of the composition.

Gloss Oil

According to one embodiment of the invention, the non-volatile oil can be a gloss oil. The oily phase of the composition according to the invention can thus comprise at least one gloss oil.

In particular, according to one embodiment, the composition can comprise a gloss oil in an amount sufficient to provide at least a make-up performance of gloss type.

Preferably, the gloss oil(s) represent from 0.1 to 80 wt. %, better still from 1 to 60 wt. % and even better still from 5 to 50 wt. % of the total weight of the first and/or of the second composition.

The gloss oil is preferably a non-volatile oil.

The gloss oil preferably has a high molecular weight in the range from 650 to 10000 g/mol, and preferably between 750 and 7500 g/mol.

The gloss oil for use in the present invention can be selected from:

lipophilic polymers such as:
polybutylenes such as INDOPOL H-100 (of molecular weight or MW=965 g/mol), INDOPOL H-300 (MW=1340 g/mol), INDOPOL H-1500 (MW=2160 g/mol) marketed or manufactured by the company AMOCO, hydrogenated polyisobutylenes such as PANALANE H-300 E marketed or manufactured by the company AMOCO (MW=1340 g/mol), VISEAL 20000 marketed or manufactured by the company SYNTEAL (MW=6000 g/mol), REWOPAL PIB 1000 marketed or manufactured by the company WITCO (MW=1000 g/mol), polydecenes and hydrogenated polydecenes such as: PURESYN 10 (MW=723 g/mol), PURESYN 150 (MW-9200 g/mol) marketed or manufactured by the company MOBIL CHEMICALS, copolymers of vinylpyrrolidone such as: vinylpyrrolidone/1-hexadecene copolymer, ANTARON V-216 marketed or manufactured by the company ISP (MW=7300 g/mol), esters such as:
esters of linear fatty acids having a total carbon number in the range from 35 to 70 such as pentaerythrityl tetrapelargonate (MW=697 g/mol), hydroxylated esters such as polyglycerol-2 triisostearate (MW=965 g/mol), aromatic esters such as tridecyl trimellitate (MW=757 g/mol), esters of fatty alcohol or of branched $C_{24}$-$C_{28}$ fatty acids such as those described in application EP-A-0 955 039, and notably triisoarachidyl citrate (MW=1033.76 g/mol), pentaerythrityl tetraisononanoate (MW=697 g/mol), glyceryl triisostearate (MM=891 g/mol), glyceryl tridecyl-2 tetradecanoate (MW=1143 g/mol), pentaerythrityl tetraisostearate (MW=1202 g/mol), polyglyceryl-2 tetraisostearate (MW=1232 g/mol) or pentaerythrityl tetradecyl-2 tetradecanoate (MW=1538 g/mol), a polyester resulting from the esterification of at least one triglyceride of hydroxylated carboxylic acid(s) by an aliphatic monocarboxylic acid and by an aliphatic dicarboxylic acid, optionally unsaturated such as castor oil, of succinic acid and of isostearic acid marketed under the reference Zenigloss by Zenitech, esters of diol dimer and of diacid dimer of general formula HO—$R^1$—(—OCO—$R^2$—COO—$R^1$—)$_h$—OH, in which:

$R^1$ represents a residue of diol dimer obtained by hydrogenation of dilinoleic diacid $R^2$ represents a residue of hydrogenated dilinoleic diacid, and h represents an integer in the range from 1 to 9, notably the esters of dilinoleic diacids and of dilinoleic dimer diols marketed by the company NIPPON FINE CHEMICAL under the trade name LUSPLAN DD-DA5® and DD-DA7®, silicone oils such as phenylated silicones (also called phenylated silicone oil) such as BELSIL PDM 1000 from the company WACKER (MW=9000 g/mol), phenyl trimethicones (such as the phenyl trimethicone sold under the trade name DC556 by Dow Corning), phenyl dimethicones, phenyl trimethylsiloxy diphenyl siloxanes, diphenyl dimethicones, diphenyl methyldiphenyl trisiloxanes;

oils of vegetable origin such as sesame oil (MW=820 g/mol), and mixtures thereof.

The gloss oil can also be an oligomer of triglyceride of hydroxylated fatty acid and of saturated diacid.

Said oligomer is obtained by reaction of a triglyceride of hydroxylated fatty acid (such as hydrogenated castor oil) and of a saturated diacid.

According to the invention, the diacid is said to be saturated when the hydrocarbon chain from which it is constituted does not have an unsaturation, i.e. a carbon-carbon double bond.

"Diacid" means a hydrocarbon compound containing two carboxyls —COOH. The diacid can be a single diacid or a mixture of several diacids.

Moreover, in the sense of the invention, the oligomer can be a mixture of several oligomers.

Among the saturated diacids that can be used, we may mention sebacic acid (or 1,10-decanedioic acid), succinic acid, adipic acid, azelaic acid, octadecamethylene dicarboxylic acid and eicosadicarboxylic acid.

More particularly, the oligomer can be an oligoester whose monomers are represented by the following formulae (A) of triglyceride and (B) of diacid:

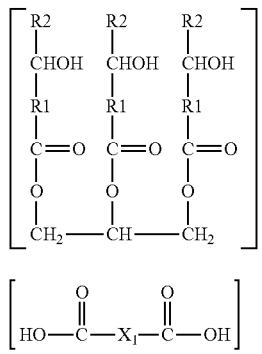

in which
$R_1$ represents a saturated or unsaturated, linear or branched alkylene group containing for example from 1 to 18 carbon atoms, and $R_2$ represents a saturated or unsaturated, linear or branched alkyl group containing for example from 1 to 12 carbon atoms;

$R_1$ preferably represents a group $(CH_2)_n$—, where n can vary from 1 to 20 and notably from 3 to 16, for example from 6 to 12;

$R_2$ preferably represents a group $(CH_2)_m CH_3$, where m can vary from 0 to 11 and notably from 2 to 11, for example from 3 to 9;

According to one embodiment n=10 and m=5, and the group

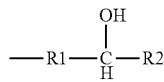

represents the alkyl residue of 12-hydroxystearic acid (the main component of hydrogenated castor oil);

$X_1$ is a linear or branched alkylene group, for example a linear alkylene group $(CH_2)_x$—, where x can vary from 1 to 30 and notably from 3 to 15.

When the diacid is sebacic acid, x is equal to 8.

The average degree of polymerization of the oligomer can vary between 3 and 12.

The oligoester of hydrogenated castor oil and of sebacic acid is notably marketed by the company CRODA under different designations depending on the degree of polymerization.

Among the oligoesters formed from hydrogenated castor oil and sebacic acid, the one with a degree of polymerization of about 4.6 is available under the trade name "CROMADOL CWS-5" and the one with a degree of polymerization of about 9.5 is available under the trade name "CROMADOL CWS-10", marketed by Croda Japan K.K.

We may also mention the oligomer of hydrogenated castor oil and sebacic acid sold under the designation CRODABOND-CSA (MW=3500) by the company CRODA.

The oligomer can be present in the composition according to the invention at a content in the range from 0.1 to 50 wt. %, particularly from 0.1 to 40 wt. %, more particularly from 0.5 to 30% and for example from to 20 wt. %, relative to the total weight of the composition.

Preferably, the gloss oil has a refractive index greater than or equal to 1.45 and notably in the range from 1.45 to 1.6.

Volatile Oil

The fatty phase of the composition according to the invention can comprise at least one volatile oil.

The term "volatile oil" means, within the meaning of the invention, an oil capable of evaporating on contact with keratinous substances in less than one hour at ambient temperature and atmospheric pressure (760 mmHg). The volatile organic solvent or solvents and the volatile oils of the invention are volatile cosmetic organic solvents and oils which are liquid at ambient temperature and which have a non-zero vapour pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 8000 Pa (0.01 to 60 mmHg).

These oils can be hydrocarbon oils, silicone oils, fluorinated oils or mixtures thereof.

a. Silicone Oil

According to a variant of the invention, the volatile oil is a volatile silicone oil.

The term "silicone oil" means an oil comprising at least one silicon atom and in particular comprising Si—O groups.

The volatile silicone oil which can be used in the invention can be selected from silicone oils having a flash point ranging from 40° C. to 102° C., preferably having a flash point of greater than 55° C. and less than or equal to 95° C. and preferably ranging from 65° C. to 95° C.

The volatile silicone oil can be selected from linear or cyclic silicone oils, such as linear or cyclic polydimethylsiloxanes (PDMSs) having from 3 to 7 silicon atoms.

Mention may be made, as examples of such oils, of octyl trimethicone, hexyl trimethicone, decamethyl-cyclopentasiloxane (cyclopentasiloxane or D5), octa-methylcyclotetrasiloxane (cyclotetradimethylsiloxane or D4), dodecamethylcyclohexasiloxane (D6), decamethyl-tetrasiloxane (L4), KF 96 A from Shin Etsu, or polydimethylsiloxanes, such as those sold under the references DC 200 (1.5 cSt), DC 200 (5 cSt) and DC 200 (3 cSt) by Dow Corning.

b. Hydrocarbon Oil

According to a variant of the invention, the volatile oil is a volatile hydrocarbon oil.

The term "hydrocarbon oil" means an oil formed essentially, indeed even composed, of carbon and hydrogen atoms and optionally of oxygen and nitrogen atoms and which does not comprise a silicon or fluorine atom. It can comprise alcohol, ester, ether, carboxylic acid, amine and/or amide groups.

The volatile hydrocarbon oils (also known as solvents) can be selected from hydrocarbon oils having from 8 to 16 carbon atoms and in particular branched $C_8$-$C_{16}$ alkanes, such as $C_8$-$C_{16}$ isoalkanes, of petroleum origin (also known as isoparaffins), such as isododecane (also known as 2,2,4,4,6-pentamethyl-heptane), isodecane, isohexadecane and, for example, the oils sold under the Isopar or Permethyl trade names, branched $C_8$-$C_{16}$ esters, isohexyl neopentanoate and mixtures thereof. Other volatile hydrocarbon oils, such as petroleum distillates, in particular those sold under the Shell Solt name by Shell, can also be used. Preferably, the volatile solvent is selected from volatile hydrocarbon oils having from 8 to 16 carbon atoms and mixtures thereof.

Mention may also be made, as other volatile hydrocarbon solvents (oils) which can be used in the composition according to the invention, of ketones which are liquid at ambient temperature, such as methyl ethyl ketone or acetone; short-chain esters (having a total of 3 to 8 carbon atoms), such as ethyl acetate, methyl acetate, propyl acetate or n-butyl acetate; ethers which are liquid at ambient temperature, such as diethyl ether, dimethyl ether or dichlorodiethyl ether; or alcohols and in particular linear or branched lower monoalcohols having from 2 to 5 carbon atoms, such as ethanol, isopropanol or n-propanol.

c. Fluorinated Oils

The volatile oil can also be selected from fluorinated oils, such as perfluoropolyethers, perfluoroalkanes, such as perfluorodecalin, perfluoro-adamantanes, monoesters, diesters and triesters of perfluoroalkyl phosphates and fluorinated ester oils.

Advantageously, the composition comprises at least one volatile oil.

Preferably, the volatile oil is a hydrocarbon oil.

Preferably, the composition exhibits a content of volatile oil of less than or equal to 50 wt. %, preferably of less than or equal to 30 wt. % and better still of less than or equal to 20 wt. %, relative to the total weight of the composition.

More preferably, the first composition is free from volatile oil.

Preferably, the composition exhibits a content of volatile silicone oil of less than or equal to 15 wt. %, preferably of less than or equal to 10 wt. % and better still of less than or equal to 5 wt. %, relative to the total weight of the composition. More preferably, the composition is free from volatile silicone oil.

2. Solid Fats

Advantageously, the oily phase of the composition according to the invention can include at least one solid fat such as a pasty fat or a wax.

Pasty Fats

"Pasty" means, in the sense of the present invention, a lipophilic fatty compound with reversible solid/liquid change of state, displaying, in the solid state, anisotropic crystalline organization, and having, at a temperature of 23° C., a liquid fraction and a solid fraction.

In other words, the initial melting point of the pasty compound can be less than 23° C. The liquid fraction of the pasty compound measured at 23° C. can represent 9 to 97 wt. % of the compound. Said fraction that is liquid at 23° C. preferably represents between 15 and 85%, more preferably between 40 and 85 wt. %.

In the sense of the invention, the melting point corresponds to the temperature of the most endothermic peak observed in thermal analysis (DSC) as described in standard ISO 11357-3; 1999. The melting point of a pasty substance or of a wax can be measured using a differential scanning calorimeter (DSC), for example the calorimeter sold under the designation "MDSC 2920" by the company TA Instruments.

The measurement protocol is as follows:

A 5 mg sample of pasty substance or wax (according to the case) placed in a crucible is submitted to a first temperature rise from −20° C. to 100° C., at a heating rate of 10° C./minute, then it is cooled from 100° C. to −20° C. at a cooling rate of 10° C./minute and is finally submitted to a second temperature rise from −20° C. to 100° C. at a heating rate of 5° C./minute. During the second temperature rise, we measure the variation of the difference in power absorbed by the empty crucible and by the crucible containing the sample of pasty substance or wax as a function of the temperature. The melting point of the compound is the value of the temperature corresponding to the top of the peak of the curve representing the variation of the difference of power absorbed as a function of the temperature.

The liquid fraction by weight of the pasty compound at 23° C. is equal to the ratio of the enthalpy of fusion consumed at 23° C. to the enthalpy of fusion of the pasty compound.

The enthalpy of fusion of the pasty compound is the enthalpy consumed by the compound in passing from the solid state to the liquid state. The pasty compound is said to be in the solid state when the whole of its mass is in crystalline solid form. The pasty compound is said to be in the liquid state when the whole of its mass is in liquid form.

The enthalpy of fusion of the pasty compound is equal to the area under the curve of the thermogram obtained using a differential scanning calorimeter (DSC), such as the calorimeter sold under the designation MDSC 2920 by the company TA Instruments, with a temperature rise of 5 or 10° C. per minute, according to standard ISO 11357-3:1999. The enthalpy of fusion of the pasty compound is the amount of energy required to cause the compound to change from the solid state to the liquid state. It is expressed in J/g.

The enthalpy of fusion consumed at 23° C. is the amount of energy absorbed by the sample on changing from the solid state to the state that it exhibits at 23° C. constituted of a liquid fraction and of a solid fraction.

The liquid fraction of the pasty compound measured at 32° C. preferably represents from 30 to 100 wt. % of the compound, preferably from 50 to 100%, more preferably from 60 to 100 wt. % of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the enthalpy of fusion consumed at 32° C. to the enthalpy of fusion of the pasty compound. The enthalpy of fusion consumed at 32° C. is calculated in the same way as the enthalpy of fusion consumed at 23° C.

The pasty compound is preferably selected from synthetic compounds and compounds of vegetable origin. A pasty compound can be obtained by synthesis from starting products of vegetable origin.

The pasty compound is advantageously selected from
  lanolin and its derivatives
  polyol ethers selected from ethers of pentaerythritol and of polyalkylene glycol, ethers of fatty alcohol and of sugar, and mixtures thereof, ether of pentaerythritol and polyethylene glycol having 5 oxyethylenated units (5 EO) (CTFA name: PEG-5 Pentaerythrityl Ether), ether of pentaerythritol and polypropylene glycol having 5 oxypropylenated units (5 PO) (CTFA name: PPG-5 Pentaerythrityl Ether), and mixtures thereof and more especially the mixture PEG-5 Pentaerythrityl Ether, PPG-5 Pentaerythrityl Ether and soybean oil, marketed under the designation "Lanolide" by the company Vevy, the constituents of said mixture being in the proportions by weight 46/46/8: 46% of PEG-Pentaerythrityl Ether, 46% of PPG-5 Pentaerythrityl Ether and 8% of soybean oil.
  silicone compounds, polymeric or otherwise
  fluorinated compounds, polymeric or otherwise
  vinylic polymers, notably:
    homopolymers of olefins (such as polyvinyl laurate)
    copolymers of olefins
    homopolymers and copolymers of hydrogenated dienes linear or branched oligomers, homo- or copolymers of alkyl (meth)acrylates preferably having a $C_8$-$C_{30}$ alkyl group homo- and copolymeric oligomers of vinyl esters having $C_8$-$C_{30}$ alkyl groups homo- and copolymeric oligomers of vinyl ethers having $C_8$-$C_{30}$ alkyl groups, fat-soluble polyethers resulting from polyetherification between one or more C2-C100, preferably C2-C50, diols, esters, and/or mixtures thereof.

The pasty compound is preferably a polymer, notably a hydrocarbon polymer.

Among the fat-soluble polyethers, particular preference is given to the copolymers of ethylene oxide and/or of propylene oxide with $C_6$-$C_{30}$ long-chain alkylene oxides, more preferably such that the weight ratio of the ethylene oxide and/or propylene oxide to alkylene oxides in the copolymer is from 5:95 to 70:30. In this class, we may notably mention copolymers such that the long-chain alkylene oxides are arranged in blocks having an average molecular weight from 1000 to 10 000, for example a polyoxyethylene/polydodecyl glycol block copolymer such as the ethers of dodecanediol (22 mol) and of polyethylene glycol (45 EO) marketed under the brand name ELFACOS ST9 by Akzo Nobel.

Among the esters, notably the following are preferred:

the esters of an oligomeric glycerol, notably the esters of diglycerol, in particular the condensates of adipic acid and of glycerol, for which a proportion of the hydroxyl groups of the glycerols have reacted with a mixture of fatty acids such as stearic acid, capric acid, stearic acid and isostearic acid and 12-hydroxystearic acid, notably such as those marketed under the brand name Softisan 649 by the company Sasol the arachidyl propionate marketed under the brand name Waxenol 801 by Alzo, the esters of phytosterol, the triglycerides of fatty acids and their derivatives the esters of pentaerythritol the non-crosslinked polyesters resulting from polycondensation between a dicarboxylic acid or a linear or branched C4-C50 polycarboxylic acid and a diol or a C2-C50 polyol, the aliphatic esters of ester resulting from the esterification of an ester of aliphatic hydroxycarboxylic acid by an aliphatic carboxylic acid.

The aliphatic carboxylic acid has from 4 to 30 and preferably from 8 to 30 carbon atoms. It is preferably selected from hexanoic acid, heptanoic acid, octanoic acid, ethyl-2 hexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid, docosanoic acid, and mixtures thereof.

The aliphatic carboxylic acid is preferably branched.

The ester of aliphatic hydroxycarboxylic acid is advantageously derived from an aliphatic hydroxylated carboxylic acid having from 2 to 40 carbon atoms, preferably from 10 to 34 carbon atoms and more preferably from 12 to 28 carbon atoms, and from 1 to 20 hydroxyl groups, preferably from 1 to 10 hydroxyl groups and more preferably from 1 to 6 hydroxyl groups. The ester of aliphatic hydroxycarboxylic acid is selected from:

a) the partial or total esters of saturated linear monohydroxylated aliphatic monocarboxylic acids;

b) the partial or total esters of unsaturated monohydroxylated aliphatic monocarboxylic acids;

c) the partial or total esters of saturated monohydroxylated aliphatic polycarboxylic acids;

d) the partial or total esters of saturated polyhydroxylated aliphatic polycarboxylic acids;

e) the partial or total esters of $C_2$ to $C_{16}$ aliphatic polyols that have reacted with a mono- or polyhydroxylated aliphatic mono- or polycarboxylic acid, and mixtures thereof.

The aliphatic esters of ester are advantageously selected from:

the ester resulting from the reaction of esterification of hydrogenated castor oil with isostearic acid in the proportions 1 to 1 (1/1) or monoisostearate of hydrogenated castor oil, the ester resulting from the reaction of esterification of hydrogenated castor oil with isostearic acid in the proportions 1 to 2 (1/2) or the diisostearate of hydrogenated castor oil, the ester resulting from the reaction of esterification of hydrogenated castor oil with isostearic acid in the proportions 1 to 3 (1/3) or triisostearate of hydrogenated castor oil, and mixtures thereof.

According to a first embodiment, the pasty compound or compounds preferably represent 0.1 to 80%, better 0.5 to 60%, better 1 to 30% and better still 1 to 20 wt. % of the composition.

According to a second embodiment, the composition is free from pasty fats.

Wax(es)

According to one embodiment of the invention, the composition includes at least one wax.

The wax considered within the scope of the present invention is generally a lipophilic compound, solid at room temperature (25° C.), with reversible solid/liquid change of state, having a melting point greater than or equal to 30° C. which can be up to 200° C. and notably up to 120° C.

In particular, the waxes suitable for the invention can have a melting point greater than or equal to 45° C., and in particular greater than or equal to 55° C.

The waxes that can be used in the compositions according to the invention are selected from waxes, solid at room temperature, of animal, vegetable, mineral or synthetic origin and mixtures thereof.

As examples illustrating the waxes suitable for the invention, we may notably mention the hydrocarbon waxes such as beeswax, lanolin wax, and insect waxes from China, rice bran wax, carnauba wax, candelilla wax, ouricury wax, alpha wax, berry wax, shellac wax, Japan wax and sumac wax; montan wax, waxes of orange and of lemon, microcrystalline waxes, paraffins and ozokerite; polyethylene waxes, waxes obtained by Fischer-Tropsch synthesis and waxy copolymers as well as their esters.

We may also mention waxes obtained by catalytic hydrogenation of animal or vegetable oils having linear or branched, $C_8$-$C_{32}$ fatty chains. Among the latter, we may notably mention isomerized jojoba oil such as the partially hydrogenated trans isomerized jojoba oil manufactured or marketed by the company DESERT WHALE under the trade reference Iso-Jojoba-50®, hydrogenated sunflower oil, hydrogenated castor oil, hydrogenated copra oil, hydrogenated lanolin oil, and di-(trimethylol-1,1,1 propane) tetrastearate sold under the designation Hest 2T-4S® by the company HETERENE.

We may also mention the silicone waxes ($C_{30-45}$ ALKYL DIMETHICONE), and the fluorinated waxes.

It is also possible to use the waxes obtained by hydrogenation of castor oil esterified with cetyl alcohol sold under the names Phytowax ricin [castor] 16L64® and 22L73® by the company SOPHIM. Said waxes are described in application FR-A-2792190.

The wax used can be a $C_{20}$-$C_{40}$ alkyl (hydroxystearyloxy) stearate (the alkyl group having from 20 to 40 carbon atoms), alone or in a mixture.

A wax of this kind is notably sold under the names "Kester Wax K 82 P®", "Hydroxypolyester K 82 P®" and "Kester Wax K 80 P®" by the company KOSTER KEUNEN.

As micro waxes that can be used in the compositions according to the invention, we may notably mention the carnauba micro waxes such as that marketed under the designation MicroCare 350® by the company MICRO POWDERS, the micro waxes of synthetic wax such as that marketed under the designation MicroEase 114S® by the company MICRO POWDERS, the micro waxes constituted of a mixture of carnauba wax and of polyethylene wax such as those marketed under the names Micro Care 300® and 310® by the company MICRO POWDERS, the micro waxes constituted of a mixture of carnauba wax and synthetic wax such as that marketed under the designation Micro Care 325® by the company MICRO POWDERS, the polyethylene micro waxes such as those marketed under the names Micropoly 200®, 220®, 220L® and 250S® by the company MICRO POWDERS and the polytetrafluoroethylene micro waxes such as those marketed under the names Microslip 519® and 519 L® by the company MICRO POWDERS.

According to a first embodiment, the composition according to the invention can include a content of waxes in the range from 0.1 to 30 wt. % relative to the total weight of the composition, in particular it can contain from 0.5 to 20%, more particularly from 1 to 15%.

According to another embodiment, the composition according to the invention is wax-free.

Additives

The composition of the invention can additionally include any supplementary additive usually employed in cosmetics, such as water, antioxidants, preservatives, colorants, neutralizing agents, structurizing and thickening agents such as plasticizers, film-forming polymers, lipophilic gelling agents or non-aqueous liquid compounds, aqueous phase gelling agents, dispersants, cosmetic actives.

These additives, with the exception of water which can represent from 0 to 70 wt. % and for example from 1 to 50 and better still from 1 to 10% of the total weight of the composition, can be present in the composition at the rate of 0.0005 to 20% of the total weight of the composition and better still from 0.001 to 10%.

Structurizing/Thickening Agent

The composition of the product according to the invention can comprise, in addition to the liquid polyester obtained by condensation of unsaturated fatty acid dimer and/or trimer and diol and/or the waxes that are optionally present, a structuring agent selected from the semicrystalline polymers, the lipophilic gelling agents and mixtures thereof.

The liquid polyester obtained by condensation of unsaturated fatty acid dimer and/or trimer and diol thus makes it possible to structure the oily phase of the cosmetic composition described above. Advantageously, the composition according to the invention is preferably free from lipophilic gelling agent. Nevertheless, it can comprise at the most 10 wt. % thereof, relative to the weight of the composition. According to a particular aspect, the composition comprises less than 6 wt. %, indeed even less than 2 wt. %, of lipophilic gelling agent, relative to the total weight of the composition.

Semicrystalline Polymers

"Semicrystalline polymer" means compounds having at least two repeating units, preferably at least 3 repeating units and more especially at least 10 repeating units. "Semicrystalline polymer" means polymers having a crystallizable moiety, a crystallizable pendant chain or a crystallizable sequence in the backbone, and an amorphous moiety in the backbone and displaying a reversible first-order phase transition temperature, in particular a melting point (solid-liquid transition). When the crystallizable moiety is in the form of a crystallizable sequence of the polymer backbone, the amorphous moiety of the polymer is in the form of an amorphous sequence; the semicrystalline polymer is in this case a block copolymer for example of the diblock, triblock or multiblock type, containing at least one crystallizable block and at least one amorphous block. "Block" generally means at least 5 identical repeating units. The crystallizable block or blocks are then of a chemical nature different from the amorphous block or blocks.

The semicrystalline polymer has a melting point greater than or equal to 30° C. (notably in the range from 30° C. to 80° C.), preferably in the range from 30° C. to 60° C. This melting point is a first-order phase transition temperature.

This melting point can be measured by any known method and in particular using a differential scanning calorimeter (DSC).

Advantageously, the semicrystalline polymer or polymers to which the invention relates has a number-average molecular weight greater than or equal to 1000. Advantageously, the semicrystalline polymer or polymers of the composition of the invention have a number-average molecular weight Mn in the range from 2000 to 800 000, preferably from 3000 to 500 000, better still from 4000 to 150 000, notably less than 100 000, and preferably from 4000 to 99 000. Preferably, they have a number-average molecular weight greater than 5600, ranging for example from 5700 to 99 000. "Crystallizable chain or block" means, in the sense of the invention, a chain or block which if it were alone would pass from the amorphous state to the crystalline state, reversibly, depending on whether we are above or below the melting point. A chain in the sense of the invention is a group of atoms, pendant or lateral relative to the backbone of the polymer. A block is a group of atoms belonging to the backbone, said group constituting one of the repeating units of the polymer. Advantageously, the "crystallizable pendant chain" can be a chain having at least 6 carbon atoms.

The semicrystalline polymer can be selected from the block copolymers having at least one crystallizable block and at least one amorphous block, the homopolymers and the copolymers bearing at least one crystallizable side chain per repeating unit, and mixtures thereof.

Such polymers are described for example in document EP 1396259.

According to a more particular embodiment of the invention, the polymer is derived from a crystallizable-chain monomer selected from the saturated $C_{14}$ to $C_{22}$ alkyl (meth)acrylates.

As a particular example of structurizing semicrystalline polymer that can be used in the composition according to the invention, we may mention the products Intelimer® from the company Landec described in the brochure "Intelimer® polymers", Landec IP22 (Rev. 4-97). These polymers are solid at room temperature (25° C.). They bear crystallizable side chains and have the aforementioned formula X.

Lipophilic Gelling Agents

The lipophilic gelling agents that can optionally be used in small amounts in the composition according to the invention can be organic or inorganic, polymeric or molecular lipophilic gelling agents. However, their proportion in the composition according to the invention is limited since said composition is preferably free from additional lipophilic gelling agent or comprises at the most 10 wt. % thereof, relative to the total weight of the composition.

As inorganic lipophilic gelling agents, we may mention clays, optionally modified, such as the hectorites modified with a $C_{10}$ to $C_{22}$ ammonium chloride, such as hectorite modified with distearyl dimethyl ammonium chloride, for example that marketed under the designation Bentone 38V® by the company ELEMENTIS.

We may also mention pyrogenic silica optionally with hydrophobic surface treatment with particle size of less than 1 μm. It is in fact possible to modify the surface of the silica chemically, by chemical reaction causing a decrease in the number of silanol groups present on the surface of the silica. We can notably replace the silanol groups with hydrophobic groups: we then obtain a hydrophobic silica. The hydrophobic groups can be:

- trimethylsiloxyl groups, which are notably obtained by treatment of pyrogenic silica in the presence of hexamethyldisilazane. Silicas so treated are designated "Silica silylate" according to the CTFA (8th edition, 2000). They are for example marketed under the references Aerosil R812® by the company DEGUSSA, CAB-O-SIL TS-530® by the company CABOT,
- dimethylsilyloxyl or polydimethylsiloxane groups, which are notably obtained by treatment of pyrogenic silica in the presence of polydimethylsiloxane or dimethyldichlorosilane. Silicas so treated are designated "Silica dimethyl silylate" according to the CTFA (8th edition, 2000). They are for example marketed under the references Aerosil R972®, and Aerosil R974® by the company DEGUSSA, CAB-O-SIL TS-610® and CAB-O-SIL TS-720® by the company CABOT.

The hydrophobic pyrogenic silica has in particular a particle size that can be nanometric to micrometric, for example approximately in the range from 5 to 200 nm.

The organic polymeric lipophilic gelling agents are for example the partially or fully crosslinked elastomeric organopolysiloxanes, of three-dimensional structure, such as those marketed under the names KSG6®, KSG16® and KSG18® by the company SHIN-ETSU, Trefil E-505C® and Trefil E-506C® by the company DOW-CORNING, Gransil SR-CYC®, SR DMF10®, SR-DC556®, SR 5CYC Gel®, SR DMF 10 Gel® and SR DC 556 Gel® by the company GRANT INDUSTRIES, SF 1204® and JK 113® by the company GENERAL ELECTRIC; ethylcellulose such as that sold under the designation Ethocel® by the company DOW CHEMICAL; the galactomannans having from one to six, and in particular from two to four, hydroxyl groups per monosaccharide unit, substituted with a saturated or unsaturated alkyl chain, such as the guar gum alkylated with $C_1$ to $C_6$, and in particular $C_1$ to $C_3$ alkyl chains, and mixtures thereof; the "diblock", "triblock" or "radial" block copolymers of the polystyrene/polyisoprene, polystyrene/polybutadiene type such as those marketed under the designation Luvitol HSB® by the company BASF, of the polystyrene/copoly(ethylene-propylene) type such as those marketed under the designation Kraton® by the company SHELL CHEMICAL CO or of the polystyrene/copoly(ethylene-butylene) type, mixtures of triblock and radial (star) copolymers in isododecane such as those marketed by the company PENRECO under the designation Versagel®, for example the mixture of butylene/ethylene/styrene triblock copolymer and ethylene/propylene/styrene star copolymer in isododecane (Versagel M 5960).

As lipophilic gelling agent, we may also mention the polymers of weight-average molecular weight less than 100 000, having a) a polymer backbone having hydrocarbon repeating units having at least one heteroatom, and optionally b) at least one pendant fatty chain and/or at least one terminal fatty chain, optionally functionalized, having from 6 to 120 carbon atoms and being bound to said hydrocarbon units, as described in applications WO-A-02/056847, WO-A-02/47619 whose content is incorporated as reference; in particular the polyamide resins (notably containing alkyl groups having from 12 to 22 carbon atoms) such as those described in U.S. Pat. No. 5,783,657 whose content is incorporated as reference.

Among the lipophilic gelling agents that can be used in the compositions according to the invention, we may also mention the esters of dextrin and fatty acid, such as the dextrin palmitates, notably such as those marketed under the names Rheopearl TL® or Rheopearl KL® by the company CHIBA FLOUR.

It is also possible to use the silicone polyamides of the polyorganosiloxane type such as those described in documents U.S. Pat. No. 5,874,069, U.S. Pat. No. 5,919,441, U.S. Pat. No. 6,051,216 and U.S. Pat. No. 5,981,680.

These silicone polymers can belong to the following two families:

- polyorganosiloxanes having at least two groups capable of establishing hydrogen interactions, said two groups being located in the polymer chain, and/or
- polyorganosiloxanes having at least two groups capable of establishing hydrogen interactions, said two groups being located on grafts or branchings.

Film-Forming Agent

The composition according to the invention can include at least one film-forming polymer. "Polymer" means, in the sense of the invention, a compound having at least 2 repeating units, and preferably at least 3 repeating units.

"Film-forming polymer" means a polymer that is able to form, on its own or in the presence of a film-forming auxiliary, a macroscopically continuous film on a substrate, notably on keratinous substances.

The polymer can be present in the composition at a content in the range from 0.1 to 60 wt. %, relative to the total weight of the composition, preferably in the range from 0.1 to 50 wt. %, preferably in the range from 0.5 to 40 wt. %, more preferably in the range from 1 to 30 wt. %, and even more preferably in the range from 1 to 25 wt. %.

In one embodiment, the film-forming organic polymer is at least one polymer selected from the group comprising:

- film-forming polymers soluble in an organic liquid medium, in particular fat-soluble polymers, when the organic liquid medium contains at least one oil;
- film-forming polymers dispersible in an organic solvent medium, in particular polymers in the form of non-aqueous dispersions of polymer particles, preferably dispersions in silicone or hydrocarbon oils; in one embodiment, the non-aqueous polymer dispersions contain polymer particles stabilized on their surface by at least one stabilizing agent;
- film-forming polymers in the form of aqueous dispersions of polymer particles, often called "latex"; in this case, the composition includes an aqueous phase; and
- water-soluble film-forming polymers; in this case, the composition includes an aqueous phase.

Among the film-forming polymers that can be used in the composition of the present invention, we may mention synthetic polymers, of radical type or of polycondensate type, polymers of natural origin and mixtures thereof. As film-forming polymer, we may mention in particular acrylic polymers, polyurethanes, polyesters, polyamides, polyureas, silicone polymers, silicone grafted acrylic polymers, polyamide polymers and copolymers, polyisoprenes.

According to one example of application of the invention, the film-forming polymer is a film-forming linear ethylenic block polymer, preferably containing at least one first block and at least one second block having different glass transition temperatures (Tg), said first and second blocks being joined together by an intermediate block comprising at least one monomer that is a constituent of the first block and at least one monomer that is a constituent of the second block (these polymers are commonly called pseudo-block polymers).

Advantageously, the first and second blocks of the block polymer are incompatible with one another.

Polymers of this kind are described for example in documents EP 1411069 or WO04/028488.

We may also mention the silicone resins, generally soluble or swellable in silicone oils, which are crosslinked polyorganosiloxane polymers. The nomenclature of the silicone resins is known by the name "MDTQ", the resin being described according to the various siloxane monomer units that it contains, each of the letters "MDTQ" characterizing a type of unit.

As examples of commercially available polymethylsilsesquioxane resins, we may mention those that are marketed:

by the company Wacker under the reference Resin MK such as Belsil PMS MK:
by the company SHIN-ETSU under the references KR-220L.

As siloxysilicate resins, we may mention trimethylsiloxysilicate (TMS) resins such as that marketed under the reference SR1000 by the company General Electric or under the reference TMS 803 by the company Wacker. We may also mention the trimethylsiloxysilicate resins marketed in a solvent such as cyclomethicone, sold under the designation "KF-7312J" by the company Shin-Etsu, "DC 749", "DC 593" by the company Dow Corning.

We may also mention copolymers of silicone resins such as those mentioned above with polydimethylsiloxanes, such as the pressure-sensitive adhesive copolymers marketed by the company Dow Corning under the reference BIO-PSA and described in document U.S. Pat. No. 5,162,410 or the silicone copolymers resulting from reaction of a silicone resin, such as those described above, and of a diorganosiloxane, as described in document WO 2004/073626.

The composition according to the invention can include a plasticizer promoting the formation of a film with the film-forming polymer. Said plasticizer can be selected from all the compounds known by a person skilled in the art as being able to fulfil the required function.

Fillers

The composition according to the invention can include at least one filler, notably at a content in the range from 0.01% to 50 wt. %, relative to the total weight of the composition, preferably in the range from 0.01% to 30 wt. %. The term "fillers" means particles of any shape, colourless or white, mineral or synthetic, insoluble in the medium of the composition regardless of the temperature at which the composition is manufactured. These fillers serve notably for modifying the rheology or the texture of the composition.

The fillers can be mineral or organic of any shape, as plates, spherical or oblong, regardless of the crystallographic form (for example lamellar, cubic, hexagonal, orthorhombic, etc). We may mention talc, mica, silica, kaolin, polyamide powders (Nylon®) (Orgasol® from Atochem), poly-β-alanine and polyethylene, powders of tetrafluoroethylene polymers (Teflon®), lauroyl-lysine, starch, boron nitride, hollow polymeric microspheres such as those of polyvinylidene chloride/acrylonitrile such as Expancel® (Nobel Industrie), acrylic acid copolymers (Polytrap®) from the company Dow Corning) and silicone resin microbeads (Tospearls® from Toshiba, for example), particles of elastomeric polyorganosiloxanes, precipitated calcium carbonate, magnesium carbonate and hydrocarbonate, hydroxyapatite, hollow silica microspheres (Silica Beads® from Maprecos), glass or ceramic microcapsules, metal soaps derived from organic carboxylic acids having from 8 to 22 carbon atoms, preferably from 12 to 18 carbon atoms, for example zinc, magnesium or lithium stearate, zinc laurate, magnesium myristate.

Colouring Matter

The composition according to the invention contains at least one colorant (also called "colouring matter"), which can be selected notably from water-soluble or fat-soluble dyes, pigments, nacres, glitter and mixtures thereof.

"Pigments" means white or coloured, mineral or organic particles, insoluble in an aqueous solution, intended to colour and/or opacify the resultant film.

The pigments can be present at a rate from 0.01 to 20 wt. %, notably from 0.01 to 15 wt. %, and in particular from 0.02 to 10 wt. %, relative to the total weight of the cosmetic composition.

Goniochromatic Colorants

The composition according to the invention can contain at least one goniochromatic colorant, which can have magnetic properties if necessary.

"Goniochromatic colorant" denotes, in the sense of the present invention, a colorant able to give, when the composition is spread out on a substrate, a colour path in the a*b* plane of the CIE 1976 colorimetric space that corresponds to a change Dh in the hue angle h of at least 20° when the angle of observation relative to the normal is varied between 0° and 80°, for an angle of incidence of the light of 45°.

The colour path can be measured for example by means of a spectrogonioreflectometer made by INSTRUMENT SYSTEMS with the reference GON 360 GONIOMETER, after the first composition has been spread out in the fluid state with a thickness of 300 μm by means of an automatic spreader on a contrast card made by ERICHSEN with the reference Type 24/5, measurement being effected against the black background of the card.

The goniochromatic colorant can be selected for example from multilayer interference structures and liquid crystal colorants.

In the case of a multilayer structure, this can comprise for example at least two layers, each layer being made for example from at least one material selected from the group comprising the following materials: $MgF_2$, $CeF_3$, ZnS, ZnSe, Si, $SiO_2$, Ge, Te, $Fe_2O_3$, Pt, Va, $Al_2O_3$, MgO, $Y_2O_3$, $S_2O_3$, $SiO_2$, $HfO_2$, $ZrO_2$, $CeO_2$, $Nb_2O_5$, $Ta_2O_5$, $TiO_2$, Ag, Al, Au, Cu, Rb, Ti, Ta, W, Zn, $MoS_2$, cryolite, alloys, polymers and combinations thereof.

The multilayer structure may or may not have, relative to a central layer, symmetry with respect to the chemical nature of the stacked layers. Different effects are obtained, depending on the thickness and the nature of the various layers.

Examples of symmetric multilayer interference structures are for example the following structures: $Fe_2O_3/SiO_2/Fe_2O_3/SiO_2/Fe_2O_3$, a pigment having this structure being marketed under the designation SICOPEARL by the company BASF; $MoS_2/SiO_2$/mica-oxide/$SiO_2$/$MoS_2$; $Fe_2O_3/SiO_2$/mica-oxide/$SiO_2/Fe_2O_3$; $TiO_2/SiO_2/TiO_2$ and $TiO_2/Al_2O_3/TiO_2$, pigments having these structures being marketed under the designation XIRONA by the company MERCK (Darmstadt).

The liquid crystal colorants comprise for example silicones or cellulose ethers onto which mesomorphic groups are grafted. As liquid-crystal goniochromatic particles, it is possible to use for example those sold by the company CHENIX as well as those marketed under the designation HELICONE® HC by the company WACKER.

As goniochromatic colorant, it is also possible to use certain nacres, effect pigments on a synthetic substrate, notably a substrate such as alumina, silica, borosilicate, iron oxide, aluminium, or holographic interference glitter obtained from polyterephthalate film.

The ratio of the proportion by weight of the magnetic pigments to the proportion of goniochromatic colorant is for example between ¼ and 4, for example between ½ and 2, and for example close to 1.

The material can moreover contain dispersed goniochromatic fibres. Such fibres can for example have a length of less than 80 μm.

Diffracting Pigments

The composition according to the invention can contain at least one diffracting pigment, which can if necessary have magnetic properties.

"Diffracting pigment" denotes, in the sense of the present invention, a pigment capable of producing a colour change depending on the angle of observation when illuminated by white light, on account of the presence of a structure that diffracts the light.

A diffracting pigment can incorporate a diffraction grating, capable for example of diffracting an incident ray of monochromatic light in defined directions.

The diffraction grating can include a periodic unit, notably a line, the distance between two adjacent units being of the same order of magnitude as the wavelength of the incident light.

When the incident light is polychromatic, the diffraction grating will separate the various spectral components of the light and produce a rainbow effect.

Regarding the structure of diffracting pigments, reference may usefully be made to the article "*Pigments Exhibiting Diffractive Effects*" of Alberto Argoitia and Matt Witzman, 2002, Society of Vacuum Coaters, 45$^{th}$ Annual Technical Conference Proceedings 2002.

The diffracting pigment can be made with units having different profiles, notably triangular, symmetric or asymmetric, with gaps, of constant or variable width, sinusoidal.

The spatial frequency of the grating and the depth of the units will be selected according to the degree of separation of the various orders desired. The frequency can vary for example between 500 and 3000 lines per mm.

Preferably, the particles of the diffracting pigment each have a flattened shape, and notably are in the form of small plates.

One and the same particle of pigment can have two crossed diffraction gratings, perpendicular or otherwise.

The diffracting pigment can have a multilayer structure containing a layer of a reflective material, covered at least on one side with a layer of a dielectric material. The latter can endow the diffracting pigment with better rigidity and durability. The dielectric material can then be selected for example from the following materials: $MgF_2$, $SiO_2$, $Al_2O_3$, $AlF_3$, $CeF_3$, $LaF_3$, $NdF_3$, $SmF_2$, $BaF_2$, $CaF_2$, $LiF$ and combinations thereof. The reflective material can be selected for example from the metals and metal alloys as well as from the nonmetallic reflecting materials. Among the metals that can be used, we may mention Al, Ag, Cu, Au, Pt, Sn, Ti, Pd, Ni, Co, Rd, Nb, Cr and their materials, combinations or alloys. Said reflective material can, on its own, constitute the diffracting pigment, which will then be monolayered.

As a variant, the diffracting pigment can have a multilayer structure comprising a core of a dielectric material covered with a reflecting layer on at least one side, or even encapsulating the core completely. A layer of a dielectric material can also cover the reflecting layer or layers. The dielectric material used is then preferably inorganic, and can be selected for example from the metal fluorides, metal oxides, metal sulphides, metal nitrides, metal carbides and combinations thereof. The dielectric material can be in the crystalline, semicrystalline or amorphous state. The dielectric material, in this configuration, can for example be selected from the following materials: $MgF_2$, $SiO$, $SiO_2$, $Al_2O_3$, $TiO_2$, WO, AlN, BN, $B_4C$, WC, TiC, TiN, $N_4Si_3$, ZnS, glass particles, carbons of the diamond type and combinations thereof.

As a variant, the diffracting pigment can be composed of a preformed dielectric or ceramic material such as a naturally lamellar mineral, for example mica, peroskovite or talc, or synthetic lamellae formed from glass, alumina, $SiO_2$, carbon, an iron oxide/mica, mica covered with BN, BC, graphite, bismuth oxychloride, and combinations thereof.

Instead of a layer of a dielectric material, other materials that improve the mechanical properties may be suitable. Such materials can comprise silicone, metal silicides, semiconducting materials formed from elements of groups III, IV and V, metals having a cubic body-centred crystalline structure, cermet compositions or materials, semiconducting glasses, and various combinations thereof.

The diffracting pigment used can notably be selected from those described in US patent application US 2003/0031870 published on 13 Feb. 2003.

A diffracting pigment can for example have the following structure: $MgF_2/Al/MgF_2$, a diffracting pigment having this structure being marketed under the designation SPECTRAFLAIR 1400 Pigment Silver by the company FLEX PRODUCTS, or SPECTRAFLAIR 1400 Pigment Silver FG. The proportion by weight of $MgF_2$ can be between 80 and 95% of the total weight of the pigment.

The amount of diffracting pigment can vary, by weight relative to the total weight of the first composition, for example from 0.1 to 5%.

The size of the diffracting pigment can for example be between 5 and 200 μm, better still between 5 and 100 μm, for example between 5 and 30 μm.

The thickness of the particles of diffracting pigment can be less than or equal to 3 μm, better still 2 μm, for example of the order of 1 μm.

Reflective Particles

The composition according to the invention can include for example reflective particles, notably of glitter, among others, magnetic or nonmagnetic.

"Reflective particles" means, in the sense of the present invention, particles whose size, structure, notably the thickness of the layer or layers of which they are constituted and their physical and chemical natures, and the surface condition, enable them to reflect incident light. This reflection can, if necessary, be of sufficient intensity to create, on the surface of the composition or of the mixture, when the latter is applied on the substrate to be made up, superglossy points that are visible to the naked eye, i.e. points that are more luminous, which contrast with their surroundings and appear to shine.

The reflective particles can be selected in such a way as not to alter significantly the colouring effect produced by the colorants with which they are combined and more particularly so as to optimize this effect in terms of colour rendition.

They can more particularly possess a yellow, pink, red, bronze, orange, brown, gold and/or copper colour or reflection.

The reflective particles can be present in the composition at a content in the range from 0.5% to 60% relative to the total weight of the composition, notably from 1% to 30 wt. %, in particular from 3% to 10 wt. %.

These particles can have a variety of shapes, notably they can be in the form of small plates or can be globular, in particular spherical.

The reflective particles, regardless of their shape, may or may not have a multilayer structure and, in the case of a multilayer structure, for example at least one layer of uniform thickness, notably of a reflective material.

When the reflective particles do not have a multilayer structure, they can be composed for example of metal oxides, notably of oxides of titanium or of iron obtained by synthesis.

When the reflective particles have a multilayer structure, the latter can for example comprise a natural or synthetic substrate, notably a synthetic substrate at least partially coated with at least one layer of a reflective material notably of at least one metal or metallic material. The substrate can be of single material or multiple material, organic and/or inorganic.

More particularly, it can be selected from glasses, ceramics, graphite, metal oxides, aluminas, silicas, silicates, notably aluminosilicates and borosilicates, synthetic mica and mixtures thereof, this list not being exhaustive.

The reflective material can include a layer of metal or of a metallic material.

Reflective particles are described notably in documents JP-A-09188830, JP-A-10158450, JP-A-10158541, JP-A-07258460 and JP-A-05017710.

Still as examples of reflective particles comprising a mineral substrate coated with a layer of metal, we may also mention the particles having a substrate of borosilicate coated with silver, also called "white nacres".

Particles with a glass substrate covered with silver, in the form of small plates, are sold under the designation MICROGLASS METASHINE REFSX 2025 PS by the company TOYAL. Particles with a glass substrate covered with nickel/chromium/molybdenum alloy are sold under the designation CRYSTAL STAR GF 550, GF 2525 by the same company.

The reflective particles, regardless of their shape, can also be selected from particles with a synthetic substrate coated at least partially with at least one layer of at least one metallic material, notably a metal oxide, selected for example from the oxides of titanium, notably $TiO_2$, of iron notably $Fe_2O_3$, of tin, of chromium, barium sulphate and the following materials: $MgF_2$, $CrF_3$, $ZnS$, $ZnSe$, $SiO_2$, $Al_2O_3$, $MgO$, $Y_2O_3$, $SeO_3$, $SiO$, $HfO_2$, $ZrO_2$, $CeO_2$, $Nb_2O_5$, $Ta_2O_5$, $MoS_2$ and mixtures or alloys thereof.

As examples of such particles, we may mention particles having a substrate of synthetic mica covered with titanium dioxide, or particles of glass coated either with brown iron oxide, titanium oxide, tin oxide or a mixture thereof such as those sold under the brand name REFLECKS® by the company ENGELHARD.

Nacres

The composition according to the invention can include at least one nacre, magnetic or nonmagnetic.

"Nacre" is to be understood as meaning coloured particles of any shape, iridescent or non-iridescent, notably produced by certain molluscs in their shell or else synthesized and which display a colour effect by optical interference.

The nacres can be selected from the nacreous pigments such as titanium mica covered with an iron oxide, mica covered with bismuth oxychloride, titanium mica covered with chromium oxide, titanium mica covered with an organic colouring matter notably of the type mentioned previously as well as the nacreous pigments based on bismuth oxychloride. They can also be particles of mica, on the surface of which at least two successive layers of metal oxides and/or of organic colouring matter are superposed.

We may also mention, as example of nacres, natural mica covered with titanium oxide, iron oxide, natural pigment or bismuth oxychloride.

Among the nacres available on the market, we may mention the nacres TIMICA, FLAMENCO and DUOCHROME (based on mica) marketed by the company ENGELHARD, the TIMIRON nacres marketed by the company MERCK, the mica-based nacres PRESTIGE marketed by the company ECKART and the nacres based on synthetic mica SUNSHINE marketed by the company SUN CHEMICAL.

The nacres can more particularly have a yellow, pink, red, bronze, orange, brown, gold and/or copper colour or reflection.

As illustration of the nacres that can be included in the composition, we may notably mention the gold-coloured nacres notably marketed by the company ENGELHARD under the name Glossy gold 212G (Timica), Gold 222C (Cloisonne), Sparkle gold (Timica), Gold 4504 (Chromalite) and Monarch gold 233X (Cloisonne); the bronze nacres notably marketed by the company MERCK under the designation Bronze fine (17384) (Colorona) and Bronze (17353) (Colorona) and by the company ENGELHARD under the designation Super bronze (Cloisonne); the orange nacres notably marketed by the company ENGELHARD under the designation Orange 363C (Cloisonne) and Orange MCR 101 (Cosmica) and by the company MERCK under the designation Passion orange (Colorona) and Matte orange (17449) (Microna); the nacres of a brown hue notably marketed by the company ENGELHARD under the designation Nu-antique copper 340XB (Cloisonne) and Brown CL4509 (Chromalite); the nacres with a copper sheen notably marketed by the company ENGELHARD under the designation Copper 340A (Timica); the nacres with a red sheen notably marketed by the company MERCK under the designation Sienna fine (17386) (Colorona); the nacres with a yellow sheen notably marketed by the company ENGELHARD under the designation Yellow (4502) (Chromalite); the nacres of a red hue with a gold sheen notably marketed by the company ENGELHARD under the designation Sunstone G012 (Gemtone); the pink nacres notably marketed by the company ENGELHARD under the designation Tan opale G005 (Gemtone); the black nacres with a gold sheen notably marketed by the company ENGELHARD under the designation Nu antique bronze 240 AB (Timica), the blue nacres notably marketed by the company MERCK under the designation Matte blue (17433) (Microna), the white nacres with a silver sheen notably marketed by the company MERCK under the designation Xirona Silver and the orange pink green golden nacres notably marketed by the company MERCK under the designation Indian summer (Xirona) and mixtures thereof.

Organic dyes and pigments; lakes

The composition according to the invention can also include organic dyes or pigments.

The dyes can be fat-soluble or water-soluble.

The fat-soluble dyes are for example Sudan Red, DC Red 17, DC Green 6, β-carotene, soybean oil, Sudan Brown, DC Yellow 11, DC Violet 2, DC orange 5, quinoline yellow.

The water-soluble dyes are for example beetroot juice and methylene blue.

The dyes can for example represent from 0.1 to 20% of the weight of the composition, or from 0.1 to 6%, when present.

The organic lakes are organic pigments formed from a colorant fixed on a substrate.

The lakes, which are also called organic pigments, can be selected from the following materials and mixtures thereof:
carmine;
organic pigments from azo, anthraquinone, indigoid, xanthene, pyrene, quinoline, triphenylmethane, or fluorane dyes. Among the organic pigments, we may notably mention those known by the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6;
the organic lakes can be insoluble salts of sodium, of potassium, of calcium, of barium, of aluminium, of zirconium, of strontium, of titanium, acid dyes such as the azo, anthraquinone, indigoid, xanthene, pyrene, quinoline, triphenylmethane, or fluorane dyes, and said dyes can contain at least one carboxylic or sulphonic acid group.

The organic lakes can also be carried on an organic substrate such as colophony or aluminium benzoate, for example.

Among the organic lakes, we may mention in particular those known by the following names: D&C Red No. 2 Aluminium lake, D&C Red No. 3 Aluminium lake, D&C Red No. 4 Aluminium lake, D&C Red No. 6 Aluminium lake, D&C Red No. 6 Barium lake, D&C Red No. 6 Barium/Strontium lake, D&C Red No. 6 Strontium lake, D&C Red No. 6 Potassium lake, D&C Red No. 7 Aluminium lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminium lake, D&C Red No. 9 Barium lake, D&C Red No. 9 Barium/Strontium lake, D&C Red No. 9 Zirconium lake, D&C Red No. 10 Sodium lake, D&C Red No. 19 Aluminium lake, D&C Red No. 19 Barium lake, D&C Red No. 19 Zirconium lake, D&C Red No. 21 Aluminium lake, D&C Red No. 21 Zirconium lake, D&C Red No. 22 Aluminium lake, D&C Red No. 27 Aluminium lake, D&C Red No. 27 Aluminium/Titanium/Zirconium lake, D&C Red No. 27 Barium lake, D&C Red No. 27 Calcium lake, D&C Red No. 27 Zirconium lake, D&C Red No. 28 Aluminium lake, D&C Red No. 30 lake, D&C Red No. 31 Calcium lake, D&C Red No. 33 Aluminium lake, D&C Red No. 34 Calcium lake, D&C Red No. 36 lake, D&C Red No. 40 Aluminium lake, D&C Blue No. 1 Aluminium lake, D&C Green No. 3 Aluminium lake, D&C Orange No. 4 Aluminium lake, D&C Orange No. 5 Aluminium lake, D&C Orange No. 5 Zirconium lake, D&C Orange No. 10 Aluminium lake, D&C Orange No. 17 Barium lake, D&C Yellow No. 5 Aluminium lake, D&C Yellow No. 5 Zirconium lake, D&C Yellow No. 6 Aluminium lake, D&C Yellow No. 7 Zirconium lake, D&C Yellow No. 10 Aluminium lake, FD&C Blue No. 1 Aluminium lake, FD&C Red No. 4 Aluminium lake, FD&C Red No. 40 Aluminium lake, FD&C Yellow No. 5 Aluminium lake, FD&C Yellow No. 6 Aluminium lake.

The chemical materials corresponding to each of the aforementioned organic colorants are mentioned in the work "International Cosmetic Ingredient Dictionary and Handbook", 1997 Edition, pages 371 to 386 and 524 to 528, published by "The Cosmetic, Toiletry, and Fragrance Association", the contents of which are incorporated in the present application by reference.

Composite Pigments

The composition according to the invention can also contain composite pigments.

The composite pigment can notably be composed of particles comprising:
an inorganic core, magnetic or nonmagnetic;
at least one coating, at least partially, with at least one organic colouring matter.

At least one binder can advantageously contribute to the fixation of the organic colouring matter on the inorganic core.

The particles of composite pigment can be variously shaped. Said particles can notably be in the form of small plates or can be globular, in particular spherical, and can be hollow or solid. "In the form of small plates" denotes particles whose ratio of the largest dimension to the thickness is greater than or equal to 5.

A composite pigment can for example have a specific surface between 1 and 1000 $m^2/g$, notably between about 10 and 600 $m^2/g$, and in particular between about 20 and 400 $m^2/g$. The specific surface is the value measured by the BET method.

The inorganic core of the composite pigment can be of any suitable shape for fixation of particles of organic colouring matter, for example spherical, globular, granular, polyhedral, acicular, spindle-shaped, flattened in the form of flakes, rice grains, scales, as well as a combination of these forms, this list not being exhaustive.

The ratio of the largest dimension of the core to its smallest dimension can be between 1 and 50.

The inorganic core can have a size between about 1 nm and about 100 nm, or between about 5 nm and about 75 nm, for example between about 10 nm and about 50 nm.

The inorganic core can be made of a material selected from the non-exhaustive list comprising the metal salts and metal oxides, notably the oxides of titanium, of zirconium, of cerium, of zinc, of iron, ferric blue, of aluminium and of chromium, the aluminas, the glasses, the ceramics, graphite, the silicas, the silicates, notably the aluminosilicates and the borosilicates, synthetic mica, and mixtures thereof.

The oxides of titanium, notably $TiO_2$, of iron, notably $Fe_2O_3$, of cerium, of zinc and of aluminium, the silicates, notably the aluminosilicates and the borosilicates are quite particularly suitable.

The inorganic core can have a specific surface, measured by the BET method, for example between about 1 $m^2/g$ and about 1000 $m^2/g$, better still between about 10 $m^2/g$ and about 600 $m^2/g$, for example between about 20 $m^2/g$ and about 400 $m^2/g$.

The inorganic core can be coloured, if necessary.

The organic colouring matter can be as defined above.

The binder of the composite pigment can be of any type provided that it enables the organic colouring matter to adhere to the surface of the inorganic core.

The binder can notably be selected from a non-exhaustive list comprising silicone materials, polymeric, oligomeric or similar materials, and in particular from the organosilanes, the fluoroalkylated organosilanes and the polysiloxanes, for example polymethylhydrogenosiloxane, as well as various coupling agents, such as coupling agents based on silanes, titanates, aluminates, zirconates and mixtures thereof.

The colorant present in the composition can comprise a photochromic colorant or photochromic agent.

Photochromic Agents

Generally, a photochromic colorant is a colorant having the property of changing in hue when it is lit by ultraviolet light and of regaining its original colour when it is no longer illuminated by this light or of passing from a colourless state to a coloured state and vice versa. In other words, such an agent has different hues depending on whether it is illuminated by light containing a certain amount of UV radiation such as in sun light or artificial light.

We may usefully refer to the examples of photochromic agents described in EP 1 410 786.

Thermochromic Agents

It is for example possible to use the thermochromic agent marketed under the reference KROMAFAST YELLOW 5GX 02- by the company KROMACHEM Ltd.

Other Colorants

The composition according to the invention can also contain piezochromic, notably tribochromic, or solvatochromic compounds.

Actives

The composition according to the invention can include at least one additional "active". "Active" means a compound having a cosmetic and/or dermatological effect, notably on the lips.

Said active can be hydrophilic or hydrophobic. The active can be water-soluble.

Thus, the active present in the composition according to the invention can be selected independently from:
  dermorelaxants,
  agents stimulating the synthesis of dermal or epidermal macromolecules and/or preventing their degradation,
  antiglycation agents,
  anti-irritant agents,
  hydrating agents other than polyhydric alcohols and water-soluble non-ionic alkoxylated polymers,
  desquamating agents
  pigmentation-modifying agents,
  inhibitors of NO-synthase,
  agents stimulating the proliferation of fibroblasts or of keratinocytes and/or the differentiation of keratinocytes,
  anti-pollution or anti-free-radical agents,
  soothing agents,
  agents acting on the microcirculation,
  agents acting on the energy metabolism of the cells,
  cicatrizing agents, and
  mixtures thereof.

Usual Additional Cosmetic Ingredients

The composition according to the invention can additionally include any usual cosmetic ingredient, which can notably be selected from the antioxidants, perfumes, preservatives, neutralizing agents, surfactants, sun filters, vitamins, self-tanning compounds, antiwrinkle actives, emollients, anti-free-radical agents, deodorants, sequestering agents, film-forming agents, and mixtures thereof.

Of course, a person skilled in the art will take care to select any additional ingredients and/or their amount in such a way that the advantageous properties of the composition according to the invention are not, or substantially not, altered by the addition that is envisaged.

It is to be understood that the amount of these ancillary compounds can be adjusted by a person skilled in the art so as not to have an adverse effect on the effect desired within the scope of the present invention.

Cosmetic Product or Kit

The invention also relates to a make-up kit containing a composition according to the invention and is advantageously accompanied by suitable means of application. These means can be brushes, pens, pencils, felt-tip pens, sponges, tubes and/or mousse nozzles.

Form of the Composition

The applications of the composition according to the invention are multiple and relate to all cosmetic products, more particularly lipsticks or lip glosses.

The composition of the invention can be in the form of a solid, compacted or cast composition notably as a stick or in a dish, pasty or liquid. Advantageously, it is in solid form, i.e. in a hard form (not flowing under its own weight) notably cast or compacted, for example as a stick or in a dish.

It can be in the form of paste, solid or cream. It can be an oil-in-water or water-in-oil emulsion, a solid or soft anhydrous gel, or in the form of loose or compacted powder and even in a two-phase form. Preferably, it is in the form of a composition with an oily and notably anhydrous continuous phase; in this case, it can contain an aqueous phase in a proportion of less than 5%.

The composition according to the invention can be in the form of a coloured or non-coloured skin care composition, in the form of a composition for sun protection or for make-up removal or in the form of a hygiene composition. If it contains cosmetic actives, it can then be used as a base for care or non-therapeutic treatment for the skin such as the hands or the face or for the lips (lip balms, protecting the lips from the cold and/or sun and/or wind), product for artificial tanning of the skin.

The composition of the invention can also be in the form of a coloured make-up product for the skin, in particular for the face such as a foundation, a blusher or eye shadow, a concealer, a blush, a loose or compacted powder, or a make-up product for the body such as a semi-permanent tattooing product or for make-up of the lips such as a lipstick, a lip pencil or a lip gloss, optionally having properties of care or of non-therapeutic treatment, a make-up product for the integumentary appendages for example a nail varnish, a mascara, an eyeliner, a product for colouring or care of the hair.

Preferably, the composition according to the invention is in the form of a lipstick or a lip gloss.

Of course, the composition of the invention must be physiologically acceptable (in particular cosmetically acceptable), i.e. non-toxic and suitable for application on the skin, the integumentary appendages or the lips of human beings.

"Cosmetically acceptable" means of pleasant taste, feel, appearance and/or odour, applicable for several days over several months.

The composition according to the invention can be manufactured by the known methods, generally used in the cosmetics field.

The present invention also relates to a method of make-up or care of the skin, lips and/or of the integumentary appendages, comprising the application of the composition according to the invention described above on the skin, the lips and/or the integumentary appendages.

The composition according to the invention can be applied on the skin both of the face and of the scalp and of the body, of the lips, of the interior of the lower eyelids, and the integumentary appendages, such as the nails, the eyelashes, the hair, the eyebrows, or even bristles.

The invention also relates to the cosmetic use of the cosmetic composition according to the invention for improving the durability properties of a glossy make-up on the skin and/or lips and/or integumentary appendages.

The examples that follow are for the purpose of illustrating the object of the present invention non-exhaustively. The amounts are given in percentage by weight.

EXAMPLES

Example 1

Lipstick

Formula A corresponds to a composition according to the invention where the polyester used is the polymer marketed by Biosynthis under the designation Viscoplast 14436H (INCI name: dilinoleic acid/butanediol copolymer).

Formula B corresponds to a composition comprising α-D-glucopyranoside β-D-fructofuranosyl acetate 2-methyl-propanoate, which is a sucrose ester, instead of the polyester.

| Chemical name | Trade name (Supplier) | INCI name | Formula A | Formula B |
| --- | --- | --- | --- | --- |
| DI(TERT-BUTYL)-4-HYDROXYTOLUENE | NIPANOX BHT (CLARIANT) | BHT | 0.1 | 0.1 |
| ALUMINIUM LAKE OF ACID PHLOXINE ON ALUMINA (23/77) (CI: 45410:2 + 77002) | SUNCROMA RED 28 AL LAKE C14-6623 (SUN) | ALUMINIUM LAKE OF DISODIUM SALT OF PHLOXINE B ON ALUMINA, ALUMINIUM BENZOATE (CI: 45410:2 + 77002) | 1.26 | 1.26 |
| BLACK IRON OXIDE (CI: 77499) | SUNPURO BLACK IRON OXIDE C33-7001 (SUN) | BLACK IRON OXIDE (CI: 77499) | 1.36 | 1.36 |
| ALUMINIUM LAKE OF BRILLIANT YELLOW FCF ON ALUMINA (42/58) (CI: 15985:1 + 77002) | SUNCROMA FD&C YEL 6 AL LK C70-5270 (SUN) | YELLOW 6 LAKE | 2.05 | 2.05 |
| TRIGLYCERIDES OF CAPRYLIC/CAPRIC ACIDS (60/40) | MYRITOL 318 (COGNIS) | CAPRYLIC/CAPRIC TRIGLYCERIDE | 6.1 | 6.1 |
| CANDELILLA WAX | CANDELILLA WAX SP 75 G (STRAHL & PITSCH) | CANDELILLA CERA | 8 | 8 |
| CALCIUM SALT OF LITHOL RED B | UNIPURE RED LC 3079 OR (LCW) | RED 7 CI 15850 | 1.51 | 1.51 |
| RICE STARCH DECONTAMINATED BY IRRADIATION | REMY DR I (BENEO-REMY) | ORYZA SATIVA (RICE) STARCH | 1 | 1 |
| MANGO OIL, DEODORIZED, PROTECTED, REFINED | LIPEX 203 (AARHUSKARLSHAMN) | MANGIFERA INDICA (MANGO) SEED OIL | 14 | 14 |
| RUTILE TITANIUM OXIDE TREATED WITH ALUMINA/SILICA/TRIMETHYLOLPROPANE (CI: 77891) | TIPAQUE PF-671 (ISHIHARA SANGYO) | TITANIUM DIOXIDE CI 77891 | 1.82 | 1.82 |
| α-D-GLUCOPYRANOSIDE β-D-FRUCTOFURANOSYL ACETATE 2-METHYLPROPANOATE | SUSTANE SAIB FOOD GRADE KOSHER (EASTMAN CHEMICAL) | SUCROSE ACETATE ISOBUTYRATE | 0 | 40 |
| HYBRID RAPESEED OIL (TRIGLYCERIDES OF PALMITIC/STEARIC/OLEIC/LINOLEIC ACIDS 3/6.5/81/6) STAB. (CITRIC ACID: 10 PPM) | AKOREX L (AARHUSKARLSHAMN) | CANOLA OIL | 18.8 | 18.8 |
| HYDROGENATED MYRISTYL ALCOHOL AND OLIVE OIL ESTERS (MP = 48 DEGREES) | PHYTOWAX OLIVE 14L48 (SOPHIM) | HYDROGENATED MYRISTYL OLIVE ESTERS | 2 | 2 |
| HYDROGENATED STEARYL ALCOHOL AND OLIVE OIL ESTERS (MP = 57 DEGREES) | PHYTOWAX OLIVE 18 L 57 (SOPHIM) | HYDROGENATED STEARYL OLIVE ESTERS | 2 | 2 |
| HYDROGENATED POLYESTER BASED ON FATTY ACIDS AND ON BUTANEDIOL (MW: 1500) | VISCOPLAST 14436 H (BIOSYNTHIS) | DILINOLEIC ACID/BUTANEDIOL COPOLYMER | 40 | 0 |

Formula A is very glossy, very slippery and comfortable during application and after application. It is soft and creamy. It does not leave a pulling sensation on the lips.

Formula B is glossy, slows down slightly when applied, is not slippery, catches and is slightly sticky. After application, pulling sensations are experienced on the lips.

Example 2

Lip Gloss

Formula C corresponds to a composition according to the invention where the polyester used is the polymer marketed by Biosynthis under the designation Viscoplast 14436H (INCI name: dilinoleic acid/butanediol copolymer).

Formula D corresponds to a composition where the polyester is absent.

| Names (INCI EU) | Formula C | Formula D |
| --- | --- | --- |
| SILICA DIMETHYL SILYLATE | 2 | 4 |
| CI 77491 (and) CI 77492 | 0.26 | 0.26 |
| CI 77499 | 0.04 | 0.04 |
| CI 15850 | 0.23 | 0.23 |
| CI 77891 | 0.15 | 0.15 |
| OCTYLDODECANOL | q.s. for 24 | q.s. for 32 |
| PRUNUS DULCIS | 10 | 10 |
| PENTAERYTHRITYL TETRAISOSTEARATE | 5 | 5 |
| HELIANTHUS ANNUUS SEED WAX | 35 | 35 |
| DIMER DILINOLEYL DIMER DILINOLEATE | 10 | |
| DILINOLEIC ACID/BUTANEDIOL COPOLYMER | | |

Formula C is very pleasant during application, slippery to just the right extent, extremely soft and creamy. It gives a good thickness of the deposit, it is glossy, not very sticky, the film obtained on the lips is quite thick and uniform, and is effectively present on the lips.

Formula D is excessively slippery and excessively oily, it migrates, it shines and the colour is not very homogeneous after application.

Formula C exhibits a viscosity, measured on a Rheomat viscometer with a 4 spindle, of 32.2 DU (deviation units).

Formula D exhibits a viscosity, measured on a Rheomat viscometer with a 4 spindle, of 24.4 DU (deviation units).

Thus, it is apparent that the polyester used according to the invention makes it possible to increase viscosity of formula C, which comprises only 2% of silica, relative to formula D, which comprises 4% of silica.

The invention claimed is:

1. A cosmetic make-up or care composition, comprising:
   an oily phase comprising dilinoleic acid/butanediol copolymer wherein the amount of dilinoleic acid/butanediol copolymer is between 5 and 60 wt. % relative to the total weight of the composition,
   wherein the composition is free from lipophilic gelling agent or comprises at most, 10 wt. % of a lipophillic gelling agent relative to the weight of the composition.

2. The cosmetic make-up or care composition according to claim 1 further comprising at least one colorant selected from the group consisting of water-soluble or fat-soluble dyes, pigments, nacres, glitter and mixtures thereof.

3. The cosmetic make-up or care composition according to claim 1 further comprising a gloss oil.

4. A lip gloss, comprising the cosmetic make-up or care composition according to claim 1.

5. A method of make-up or care of at least one of the skin, lips and integumentary appendages, comprising:
   applying the composition according to claim 1 on the at least one of skin, lips and integumentary appendages.

6. The cosmetic make-up or care composition according to claim 1, wherein the amount of polyester is between 8 wt. % and 50 wt. % relative to the total weight of the composition.

7. The cosmetic make-up or care composition according to claim 3, wherein the gloss oil is a non-volatile oil having a molecular weight from 650 to 1000 g/mol.

8. The cosmetic make-up or care composition according to claim 3, wherein the gloss oil is selected from the group consisting of a lipophillic polymer, a copolymer of vinylpyrrolidone, an ester of a linear fatty acid having a total number of carbon atoms of from 35 to 70, a hydroxylated ester, an aromatic ester, an ester of a fatty alcohol, a polyester obtained by esterification of at least one triglyceride of a hydroxylated carboxylic acid with an aliphatic monocarboxylic acid and an aliphatic dicarboxylic acid, a silicone oil, and a vegetable oil.

9. The cosmetic make-up or care composition according to claim 3, wherein the gloss oil is an ester of a diol dimer and of a diacid dimer of formula

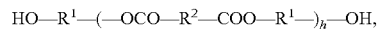

wherein
$R^1$ is a residue of diol dimer obtained by hydrogenation of dilinoleic diacid
$R^2$ is a residue of hydrogenated dilinoleic diacid, and
h is an integer in the range from 1 to 9.

10. The cosmetic make-up or care composition according to claim 3, wherein a content of the gloss oil is 0.1 to 80 wt. %.

* * * * *